United States Patent [19]

Surjaatmadja et al.

[11] Patent Number: 5,315,864

[45] Date of Patent: May 31, 1994

[54] START/STOP METHOD TO DETERMINE STATIC GEL STRENGTH

[75] Inventors: Jim B. Surjaatmadja; Bary J. Nusz; Gordon A. Turner, all of Duncan, Okla.

[73] Assignee: Halliburton Company, Duncan, Okla.

[21] Appl. No.: 43,236

[22] Filed: Apr. 6, 1993

[51] Int. Cl.⁵ ............................................. G01N 11/14
[52] U.S. Cl. ..................................................... 73/54.32
[58] Field of Search ................. 73/54.28, 54.32, 54.33, 73/54.34

[56] References Cited

U.S. PATENT DOCUMENTS

| | | |
|---|---|---|
| 2,079,247 | 5/1937 | Eckstein ............................ 73/54.33 |
| 2,122,765 | 7/1938 | Weiler . |
| 2,657,572 | 11/1953 | Fann ................................... 73/54.33 |
| 3,090,223 | 5/1963 | Juffa et al. ...................... 73/54.32 X |
| 3,269,171 | 8/1966 | Bruss et al. . |
| 3,285,057 | 11/1966 | Zurik . |
| 3,751,975 | 8/1973 | Katsura . |
| 3,803,903 | 4/1974 | Lin . |
| 3,875,791 | 4/1975 | Fitzgerald et al. . |
| 4,299,118 | 11/1981 | Gau et al. . |
| 4,466,276 | 8/1984 | Ruyak et al. . |
| 4,484,468 | 11/1984 | Gau et al. . |
| 4,622,846 | 11/1986 | Moon, Jr. et al. . |
| 4,648,264 | 3/1987 | Freese et al. . |
| 4,829,811 | 5/1989 | Ehlert et al. . |

FOREIGN PATENT DOCUMENTS

| | | | |
|---|---|---|---|
| 1236346 | 6/1986 | U.S.S.R. | ............................. 73/54.34 |
| 2066483 | 7/1981 | United Kingdom | ............... 73/54.33 |

*Primary Examiner*—Hezron E. Williams
*Assistant Examiner*—Joseph W. Roskos
*Attorney, Agent, or Firm*—Stephen R. Christian; E. Harrison Gilbert, III

[57] ABSTRACT

A method of determining static gel strength of a fluid in a container comprises: commencing relative movement between the fluid in the container and a member disposed in the fluid in the container so that torque is created; stopping the relative movement; and sensing the torque during the time between commencing and stopping the relative movement and detecting the peak torque during such time, wherein the detected peak torque defines the static gel strength of the fluid.

17 Claims, 2 Drawing Sheets

START/STOP METHOD TO DETERMINE STATIC GEL STRENGTH

BACKGROUND OF THE INVENTION

This invention relates to methods of determining static gel strength of a fluid.

Gel strength is a characteristic that represents the ability of a fluid to support particulate material mixed in the fluid. In the oil and gas industry, this is an important characteristic to know about mixtures such as cement slurries and fracturing fluids, for example, because these mixtures must be able to support their particulate material while the mixtures are placed in their respective wells. Static gel strength relates to the force required to shear an undisturbed gel. This is an important characteristic of a cement slurry used in an oil or gas well because it relates to the ability of the cement to prevent gas leaks between formations.

Consistometers and viscometers are known devices that have been used in the oil and gas industry to measure various fluid characteristics. Typically consistometers are used to measure dynamic gel strength development; however, some consistometers are equipped to measure static gel strength (see U.S. Pat. Nos. 4,622,846 to Moon, Jr. et al. and 4,648,264 to Freese et al.).

A consistometer of at least this latter type includes a container in which a sample of the fluid to be measured is placed. A paddle is disposed in the fluid in the container so that the paddle can be rotated relative to the fluid and the container. The drive shaft of an electric motor is coupled to the paddle to rotate it at a selected speed. A torque sensing device is used to sense the force with which the fluid resists the movement of the paddle.

In such a consistometer, static gel strength is measured by attempting to penetrate the fluid with the paddle rotated at a slow speed. The paddle is rotated slowly so that the undisturbed (i.e., static) fluid is sheared by the paddle. The force required to shear the fluid defines the static gel strength.

The method by which such a consistometer has been used to determine this force has been one of trial and error wherein the paddle has been continuously rotated in the fluid sample. The speed at which the paddle has been rotated has been critical to obtaining an accurate measurement of the static gel strength. On the one hand, if the speed is too fast, the fluid "breaks" and presents lower resistance to the paddle than the actual static gel strength so that a lower force than presented by the actual static gel strength is sensed. On the other hand, if the speed is too slow, the maximum force that needs to be measured just prior to breakthrough for an accurate static gel strength measurement to be obtained will never be reached. Thus, to find that speed at which the maximum force is measured takes trial and error and expert knowledge of the measurement technique and fluid.

In view of the difficulty in obtaining accurate static gel strength measurements using the foregoing method, there is the need for an improved method by which static gel strength can be more readily obtained without the need for running a static gel strength test at different speeds and without the need for an expert to perform or analyze the test.

SUMMARY OF THE INVENTION

The present invention overcomes the above-noted and other shortcomings of the prior art, and meets the aforementioned need, by providing a novel and improved method of determining static gel strength of a fluid. With the present invention, an accurate measurement of static gel strength can be readily obtained without the need for expert assistance by testing at a single selected speed at which a consistometer paddle is temporarily rotated.

In the method of the present invention, the consistometer paddle is rotated at a relatively fast speed for a short time period and then the paddle is stopped to prevent damage to the fluid at other locations in the test container. During the fast speed movement, the paddle "breaks" the fluid within a limited region of the fluid sample in the container. Torque is measured during this time period, and the maximum torque occurring just prior to breakthrough is detected to accurately define the static gel strength.

Accordingly, the present invention provides a method of determining static gel strength of a fluid in a container, comprising: commencing relative movement between the fluid in the container and a member disposed in the fluid in the container so that torque is created; stopping the relative movement; and sensing the torque during the time between commencing and stopping the relative movement and detecting the peak torque during such time, wherein the detected peak torque defines the static gel strength of the fluid. In the preferred embodiment commencing relative movement includes energizing a motor having a drive shaft coupled to the member disposed in the fluid so that the motor rotates at a selected speed, and the sensed torque is responsive to rotational lag between the member and the motor drive shaft.

Therefore, from the foregoing, it is a general object of the present invention to provide a novel and improved method of determining static gel strength of a fluid. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 5 is a flow chart of a program for controlling a computer depicted in FIG. 1 in implementing the present invention.

DETAILED DESCRIPTION OF PREFERRED EMBODIMENT

Figure 1:
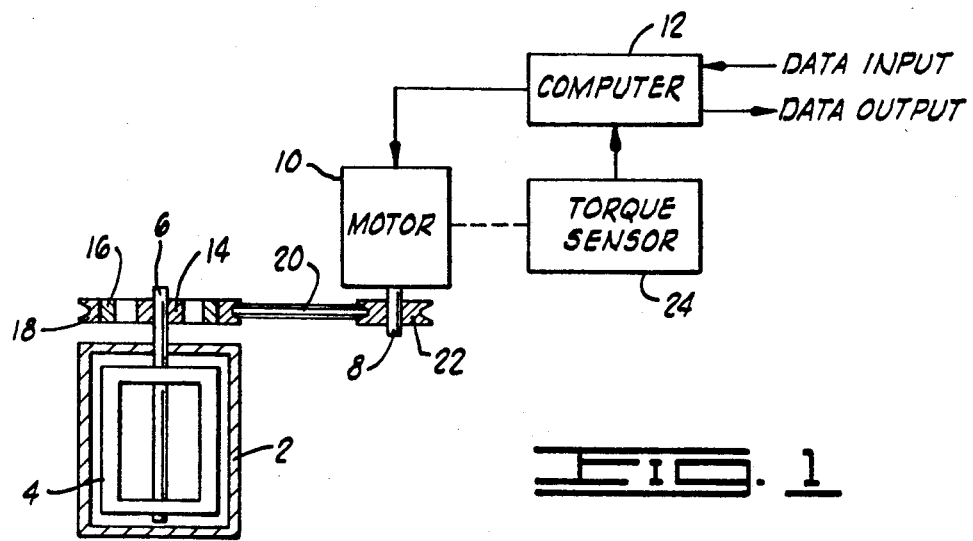
FIG. 1 is a block diagram representing components of a conventional consistometer which can be used for implementing the method of the present invention.

A conventional consistometer, for example, can be used in performing the novel and improved method of the present invention. At least part of such a consistometer is depicted in FIG. 1.

The consistometer includes a container 2 which can be closed, pressurized and heated or cooled if desired. The container 2 receives a sample of the fluid to be tested. The fluid can be any type for which static gel strength is to be measured. Examples include cement slurries and fracturing fluids used at oil or gas wells.

Rotatably received in the container 2 is a paddle 4. The paddle 4 has a shaft 6 coupled to a drive shaft 8 of an electric motor 10 so that the paddle 4 moves in a rotary manner when the motor 10 is energized. In the depicted embodiment, the motor 10 is energized in response to control by a computer 12. Suitable data input and output devices (e.g., keyboard or keypad, video display unit, printer) are connected to the computer 12.

In the preferred embodiment of the consistometer represented in FIG. 1, the coupling between the paddle shaft 6 and the drive shaft 8 is by a magnetic device having one member 14 connected to the paddle shaft 6 concentrically within, but spaced from another member 16 connected to a sheave 18 driven by a belt 20 that is also mounted on another sheave 22 connected to the motor drive shaft 8. Because of this magnetic coupling, there can be some degree of rotational lag between the angular position of the magnetic drive member 16 mechanically linked to the motor drive shaft 8 and the angular position of the magnetic drive member 14 mounted on the paddle shaft 6 when paddle rotation is commenced. This is due to the resistance or static gel strength presented by the static fluid sample to the paddle 4.

This "lag" can be somewhat analogized to a spring having one end connected to a box on a floor. When the other end of the spring is pulled, the end of the spring connected to the box and the box itself lag behind the pulled end until the frictional force between the box and the floor is overcome. This "spring-like" characteristic is an important aspect of the present invention as will be further explained hereinbelow. Accordingly, other types of couplings between the paddle 4 and motor 10 can be used so long as they initially exhibit lag until the rotary force imparted to the paddle 4 exceeds the static gel strength of the fluid sample, whereupon the paddle 4 will "break" the fluid.

The lag characteristic referred to above has an effect on the torque that is measured by a torque sensor 24 of the consistometer represented in FIG. 1. In the preferred embodiment, the torque sensor 24 is connected to the housing of the motor 10, which housing has the stator of the motor connected to it. The housing is mounted on journals so that the housing can move in response to the torque generated by the interaction between the driven paddle 4 and the static fluid in the container 2

The elements of the consistometer described above are conventional and known in the art (see, for example, U.S. Pat. Nos. 4,622,846 to Moon, Jr. et al. and 4,648,264 to Freese, et al., both incorporated herein by reference); however, the method of the present invention which can be performed using this conventional consistometer is not conventional or known.

To determine static gel strength of a fluid in accordance with the method of the present invention, a sample of the fluid to be tested is placed in the container 2 in a known manner and the consistometer is otherwise initialized in likewise conventional manner (e.g., pressurized, heated, cooled).

Relative movement between the fluid in the container 2 and the motor 10 (or other suitable member such as the paddle 4 driven by the motor 10) is commenced so that torque is created. This is done in the FIG. 1 embodiment by controlling the motor 10 with the computer 12 to operate the motor 10 at a selected speed for a limited time. In general, the motor 10 is to drive the paddle 4 as fast as possible while disturbing the fluid as little as possible. Ideally, the motor 10 should be operated to reach maximum torque, as sensed by the torque sensor 24, as quickly as possible and then the motor 10 should be immediately stopped. Although the speed and time period can be varied, a preferred speed for a particular implementation such as disclosed in the aforementioned patents is within the range between 0.1 revolution per minute and 0.5 revolution per minute for a time period within the range between 0.1 second and 5 seconds. The most preferred speed and time period presently contemplated are 0.1 revolution per minute and 1 second. The speed and time period can be selected by programming the computer 12 or by entering the desired control parameters via a suitable data input device.

At the end of the predetermined time period, the relative movement is stopped by stopping the motor 10 (e.g., deenergizing it via the computer 12). Thus, the motor 10 is started at the beginning of the time period, then it reaches and runs at the selected speed, and then it is stopped at the end of the time period. The speed used in the present invention, although faster than speeds for typical prior static gel strength tests, is still slow enough and the time period short enough that only a very small sector of the volume of the fluid sample is traversed by the paddle 4; therefore, much of the fluid is undisturbed during any one run of the present invention.

During a first part of the relative motion imparted between the fluid sample and the paddle 4, static gel strength of the fluid opposes relative movement of the paddle 4 through the fluid (this occurs until maximum torque is reached). During a second part of the relative motion, the static gel strength of the fluid is overcome (this occurs after maximum torque is reached). Stated another way, the paddle 4 moves in the fluid within the predetermined time period from at least one rotationally lagging position relative to the angular position of the drive shaft 8 of the motor 4 to a synchronized position relative to the angular position of the drive shaft 8 of the motor 10. Such differing relative positions can occur because of the action between the magnetic drive members 14, 16.

Figure 2:
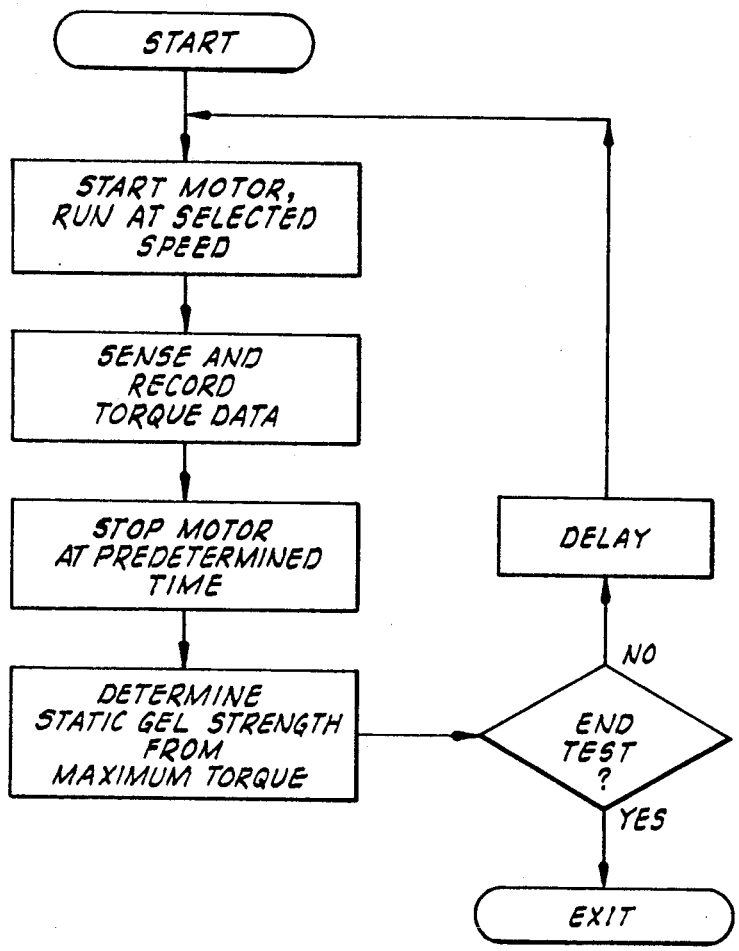
FIG. 2 is a schematic illustration of a paddle of the consistometer moving through a fluid sample in a container of the consistometer prior to the paddle breaking through the fluid by overcoming the fluid's static gel strength.
Figure 2:
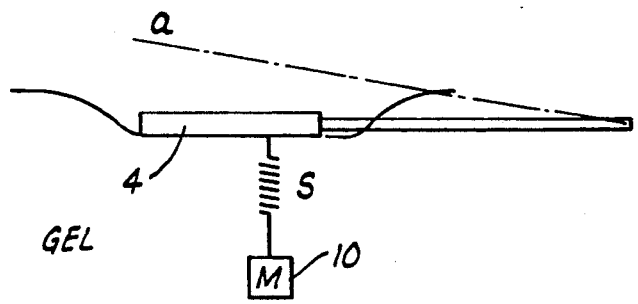
Figure 3:
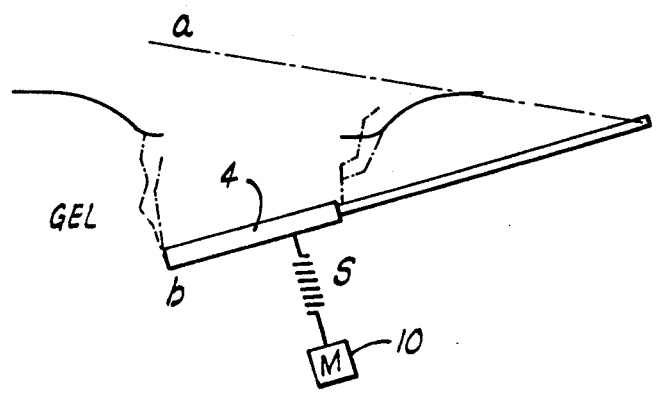
FIG. 3 is a schematic illustration of the paddle after "breakthrough."
Figure 4:
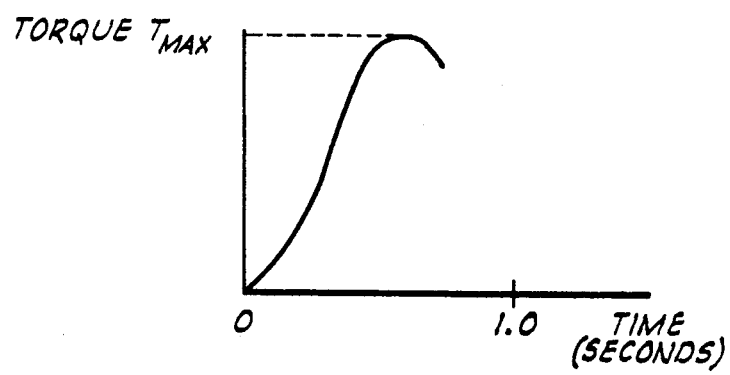
FIG. 4 is a graph illustrating torque measured by the consistometer during the time period of paddle rotation in the fluid sample.

During the time between commencing and stopping the relative movement via control of the motor 10, the torque is sensed in a conventional manner using the torque sensor 24. Electrical signals from the torque sensor 24 are provided to the computer 12, wherein data corresponding to the measured torque is recorded in the computer 12. The peak torque that occurred during the predetermined time period is detected. This maximum detected torque defines the true static gel strength of the fluid because the torque measured during this period is responsive to the strength of the fluid holding the paddle in the rotationally lagging position(s) until the strength of the static fluid is overcome and the paddle 4 attains its synchronized position relative to the angular position of the drive shaft 8. An example of a rotationally lagging position is illustrated in FIG. 2 wherein in effect the "spring" S (which represents the motor 10 force as coupled through the magnetic drive to the shaft 6 of the paddle 4) is being pulled but the paddle 4 is lagging and not shearing the fluid. That is, the paddle 4 begins to move from position "a" and the fluid initially deforms elastically, trying to resist shearing. As the motor 10 reaches its selected speed, enough force is or has been applied to the paddle 4 for it to overcome the static gel strength of the fluid, whereupon it shears the fluid as depicted in FIG. 3 (in effect, the "spring" has been sufficiently stressed so that the force created by the stressing overcomes the resisting strength or force of the fluid). After this "breakthrough", the paddle 4 quickly moves to a stable position "b" (FIG. 3) either in synchronism with the drive shaft 8 or, ultimately, at a stopped position. An illustration of sensed torque during this time is shown in FIG. 4 (torque can be equated to static gel strength in known manner).

Although the method can be implemented by performing the foregoing steps a single time, the steps can be repeated after a predetermined delay after the end of each time period during which the motor is started, run at the selected speed and then stopped. The delay is preferably within the range between 30 seconds and 60 seconds, and most preferably 60 seconds as presently contemplated.

A flow chart of a program for implementing the foregoing using the computer 12 is shown in FIG. 5. The flow chart is readily understood in view of the foregoing explanation of the method of the present invention.

Thus, the present invention is well adapted to carry out the objects and attain the ends and advantages mentioned above as well as those inherent therein. While a preferred embodiment of the invention has been described for the purpose of this disclosure, changes in the construction and arrangement of parts and the performance of steps can be made by those skilled in the art, which changes are encompassed within the spirit of this invention as defined by the appended claims.

What is claimed is:

1. A method of determining static gel strength of a fluid in a container, comprising:
    commencing relative movement between the fluid in the container and a member disposed in the fluid in the container so that torque is created;
    stopping the relative movement; and
    sensing the torque during the time between commencing and stopping the relative movement and detecting the peak torque during such time, wherein the detected peak torque defines the static gel strength of the fluid.

2. A method as defined in claim wherein commencing relative movement includes energizing a motor having a drive shaft coupled to the member disposed in the fluid so that the motor rotates at a selected speed.

3. A method as defined in claim 2, wherein the sensed torque is responsive to rotational lag between the member and the motor drive shaft.

4. A method as defined in claim 3, wherein stopping the relative movement is performed approximately one second after commencing relative movement.

5. A method as defined in claim 4, wherein the selected speed is within the range between 0.1 revolution per minute and 0.5 revolution per minute.

6. A method as defined in claim 1, wherein stopping the relative movement is performed approximately one second after commencing relative movement.

7. A method as defined in claim 1, wherein the relative movement is within the range between 0.1 revolution per minute and 0.5 revolution per minute.

8. A method of determining strength of a static fluid in a container, comprising:

operating an electric motor so that the motor starts, then runs at a selected speed and then stops, all within a predetermined time period;

driving a paddle, disposed in the fluid in the container, with the motor so that the paddle moves in the fluid within the predetermined time period from an at least one rotationally lagging position relative to the motor to a synchronized position relative to the motor; and measuring torque responsive to the strength of the fluid holding the paddle in at least one rotationally lagging position until the fluid strength is overcome and the paddle attains the synchronized position.

9. A method as defined in claim 8, further comprising determining static gel strength of the fluid in response to the maximum measured torque.

10. A method as defined in claim 9, wherein the selected speed is within the range between 0.1 revolution per minute and 0.5 revolution per minute.

11. A method as defined in claim 10, wherein the predetermined time period is within the range between 0.1 second and 5 seconds.

12. A method as defined in claim further comprising repeating said steps of operating, driving, measuring and determining beginning at a predetermined time after the end of the predetermined time period, wherein the predetermined time is within the range between 30 seconds and 60 seconds.

13. A method as defined in claim 8, wherein the selected speed is within the range between 0.1 revolution per minute and 0.5 revolution per minute.

14. A method as defined in claim 8, wherein the predetermined time period is within the range between 0.1 second and 5 seconds.

15. A method as defined in claim 8, further comprising repeating said steps of operating, driving and measuring beginning at a predetermined time after the end of the predetermined time period, wherein the predetermined time is within the range between 30 seconds and 60 seconds.

16. A method as defined in claim 8, wherein the predetermined time period can be varied.

17. A method of determining static gel strength of a fluid, comprising:
    placing a sample of the fluid in a container;
    controlling a motor with a computer to operate the motor at a selected speed within the range between 0.1 revolution per minute and 0.5 revolution per minute for a time period within the range between 0.1 second and 5 seconds, wherein the motor is started at the beginning of the time period and is stopped at the end of the time period;
    imparting, in response to operation of the motor during the predetermined time period, relative motion between the sample of fluid and a member disposed in the sample of fluid in the container so that during a first part of the relative motion static gel strength of the sample of fluid opposes relative movement of the member through the sample of fluid and so that during a second part of the relative motion the static gel strength of the sample of fluid is overcome;
    measuring torque responsive to the relative motion between the sample of fluid and the member disposed therein;
    recording in the computer data corresponding to the measured torque; and
    determining the static gel strength of the sample of fluid in response to the maximum recorded torque data.

* * * * *